United States Patent [19]

Tretout et al.

[11] Patent Number: 4,726,231

[45] Date of Patent: Feb. 23, 1988

[54] ARRANGEMENT FOR THE ULTRASONIC EXAMINATION OF OBJECTS IN LOCAL IMMERSION

[76] Inventors: Hervé Tretout, 132, Rue Boucicaut, 92260 Fontenay-aux-Roses; Philippe Pepin, 53, Rue du Temple, 75004 Paris, both of France

[21] Appl. No.: 855,749
[22] PCT Filed: Jul. 11, 1985
[86] PCT No.: PCT/FR85/00191
  § 371 Date: Mar. 12, 1986
  § 102(e) Date: Mar. 12, 1986

[30] Foreign Application Priority Data

Jul. 12, 1984 [FR] France .................................. 11076

[51] Int. Cl.$^4$ .......................................... G01N 29/00
[52] U.S. Cl. ........................................ 73/644; 73/632
[58] Field of Search ..................... 73/644, 642, 632

[56] References Cited

U.S. PATENT DOCUMENTS

| | | | |
|---|---|---|---|
| 3,255,626 | 6/1966 | Van der Veer | 73/644 |
| 3,908,445 | 9/1975 | Verdon et al. | 73/644 |
| 4,507,969 | 4/1985 | Djordjevic et al. | 73/644 |

FOREIGN PATENT DOCUMENTS 2312032 12/1976 France .................................. 73/644

*Primary Examiner*—Stewart J. Levy
*Assistant Examiner*—L. M. Arana
*Attorney, Agent, or Firm*—Watson, Cole, Grindle & Watson

[57] ABSTRACT

Arrangement for the ultrasonic examination of objects by a local immersion technique, comprising:
a source of liquid,
a pump fed by said source,
a coupling head fed with liquid by said pump and capable of directing towards the object to be examined a jet of the said liquid and a beam of ultrasonic waves which is contained in said jet and is coaxial with this jet, said coupling head comprising:
(a) a first tranquilization chamber connected to the outlet of said pump,
(b) a second cylindrical tranquilization chamber connected to the said first chamber by at least one channel for the passage of the liquid,
(c) an ultrasonic transducer capable of emitting a beam of ultrasonic waves by means of an active surface, which is directed towards the object, said active surface being situated in the second chamber, centered on the axis of said second chamber and perpendicular to this axis,
(d) a converging system coaxial with the said second chamber, the shape of which results from a calculation for the purpose of reducing or eliminating turbulence, and the outlet of which is placed at the end of the Fresnel zone relative to the transducer.

18 Claims, 10 Drawing Figures

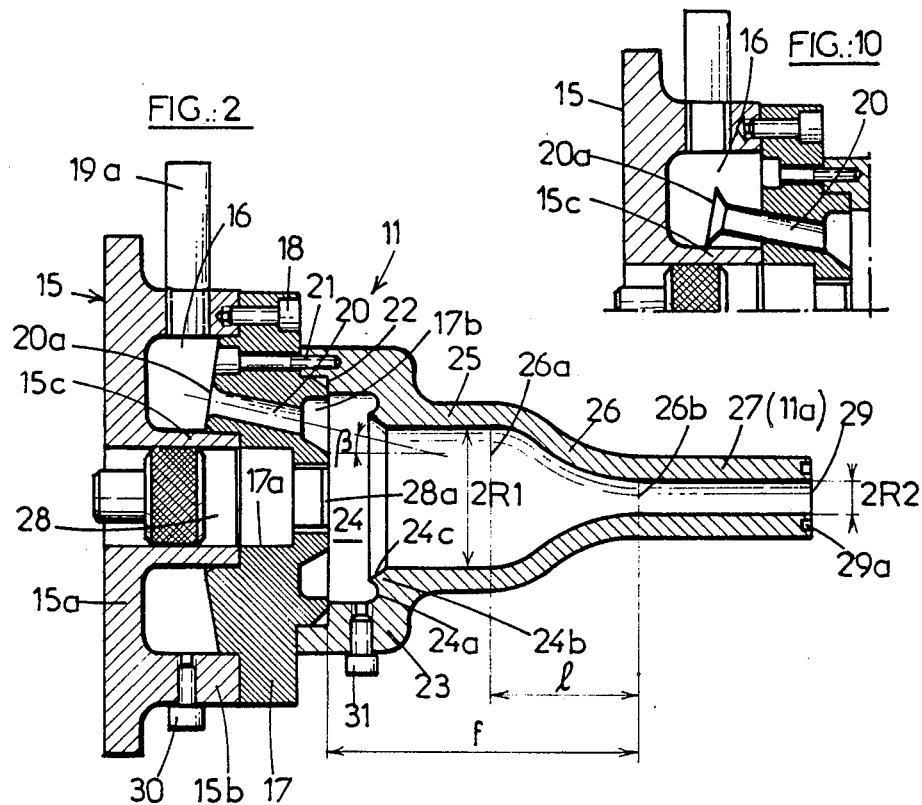
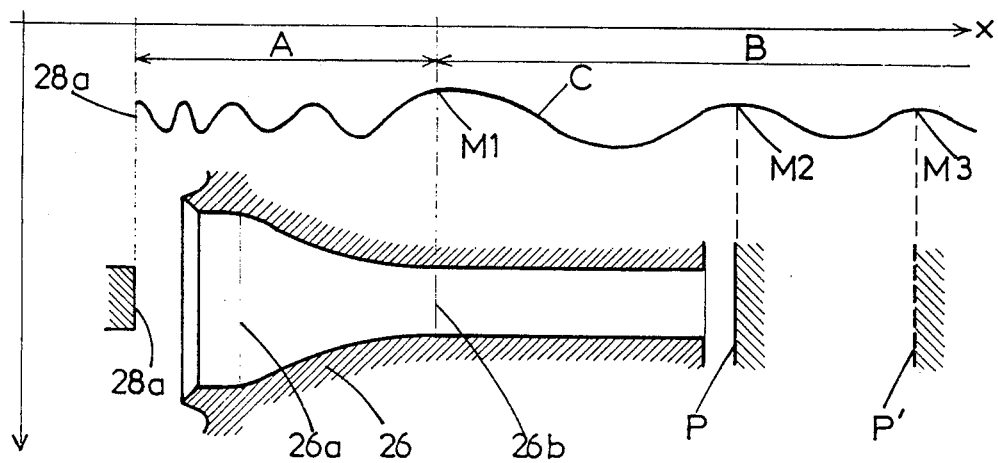

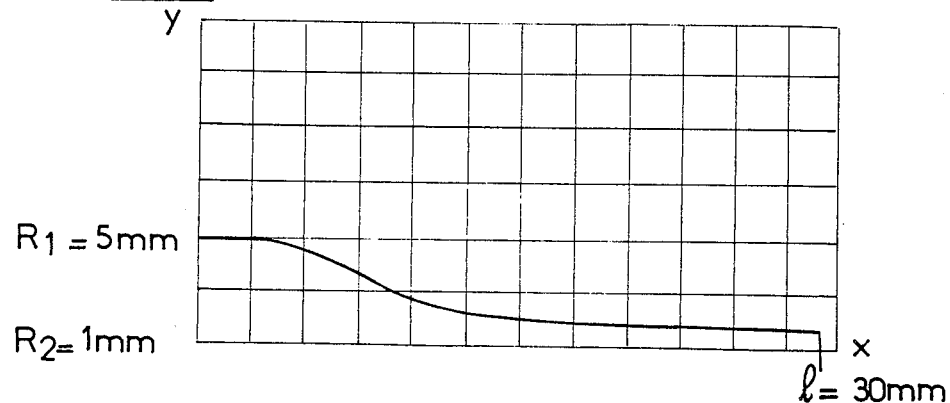
FIG.:4
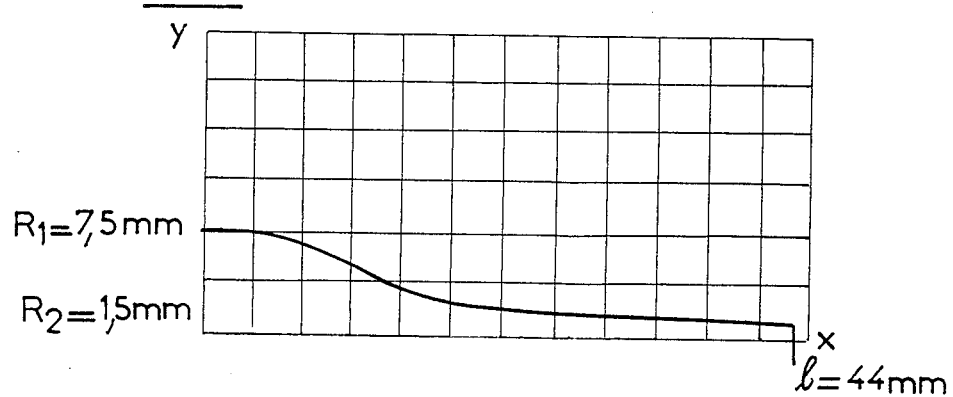
FIG.:5
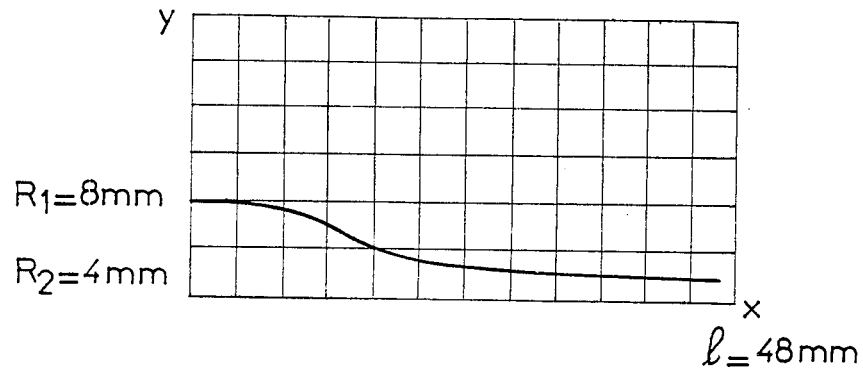
FIG.:6

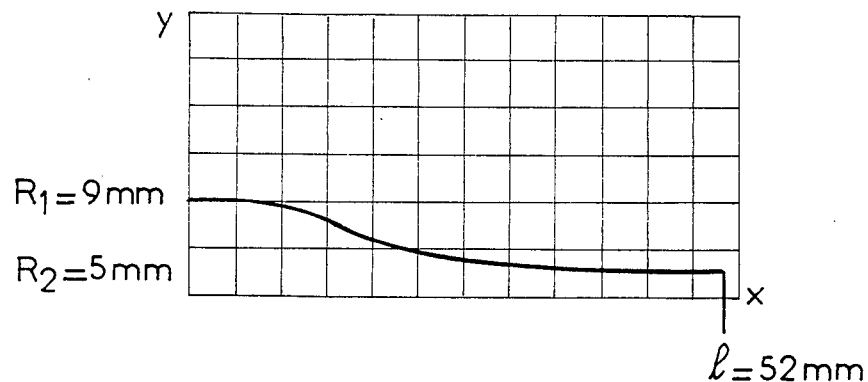
FIG.:7
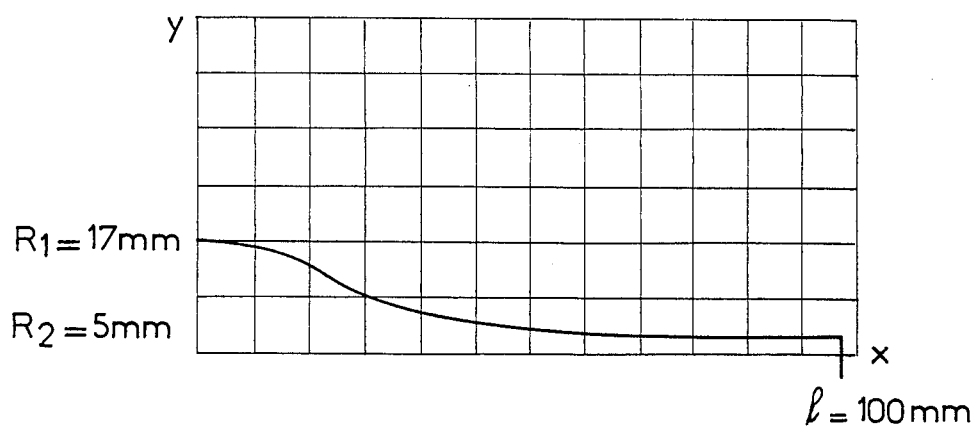
FIG.:8
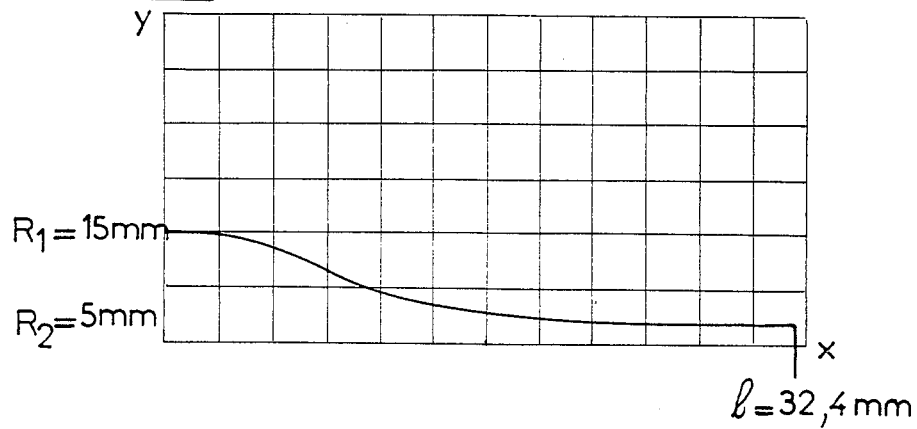
FIG.:9

ARRANGEMENT FOR THE ULTRASONIC EXAMINATION OF OBJECTS IN LOCAL IMMERSION

FIELD OF THE INVENTION

The present invention relates to an arrangement for the ultrasonic examination of objects in local immersion.

PRIOR ART

It is known that the investigation of internal defects in objects by means of a beam of ultrasonic waves is only possible with a high degree of efficiency if the ultrasonic waves are transmitted directly to the object from a layer of liquid which is in contact with the object and in which they are propagated. This result is generally obtained by immersing the object to be examined in a cell, which is generally filled with water and in which the ultrasonic transducer is likewise immersed. This method has the disadvantage of giving rise to a certain oxidation of metallic objects and to instances of water retention in objects constructed of composite materials.

In order to remedy the abovementioned disadvantages, recourse has already been had to the process referred to as "local immersion", which makes use of an arrangement comprising a hydraulic circuit with a pump, in order to produce at least one jet of liquid, more especially of water, and to direct the jet onto the object to be examined, as well as at least one ultrasonic transducer disposed in such a manner that the jet of water guides the ultrasonic waves between the transducer and the said object, a relative movement being produced between the latter and the jet of water in such a manner as to scan the various superficial zones of the object to be examined.

This process may make use either of the transmission of the ultrasonic waves through the object to be examined or of reflection thereof by its internal defects. In the first case, two jets of liquid must be directed onto opposite surfaces of the object, and ultrasonic emitter and receiver, which are distinct from one another, must be coupled with the two jets respectively. In the second case, a single ultrasonic emitter-receiver may be coupled with a single jet.

By reducing the time of contact of each superficial zone of the object to be examined with the water, the local immersion process reduces the risks of oxidation of metallic objects and of water retention in objects constructed of composite materials. Moreover, it permits examination of objects exhibiting strong absorption or having a large thickness. Finally, as the investigation of defects is based on a process of scanning the surface of the object, it requires less accurate relative positioning of the object and of the jet of water, and thus also of the ultrasonic transducer.

However, the local immersion process has not permitted detection of defects in objects with the same precision and the same certainty as the process of total immersion of a cell. This is principally due to the difficulty in obtaining a jet of water, the pressure of which is entirely stable with the passage of time. The instability of the pressure causes interference with the beam of ultrasonic waves and, consequently, fluctuations of the signal of the latter on entry thereof into the object to be examined or on exit thereof from the latter.

On the other hand, it is very difficult to avoid entirely eddies, sources of loss of ultrasonic energy, and, in consequence, of impairment of the signal-to-noise ratio, which corresponds to poor coupling between the beam of ultrasonic waves and the jet of water which guides it.

For the purpose of remedying these disadvantages, there was proposed, for example, in the U.S. Pat. No. 3,908,445 of Sept. 30, 1975 an arrangement for the ultrasonic examination of an object by a local immersion technique, comprising:

a source of liquid, a pump fed by said source, a coupling head fed with liquid by said pump and capable of directing towards the object to be examined a jet of said liquid and a beam of ultrasonic waves which is contained in said jet and is coaxial with this jet, means sensitive to the ultrasonic waves reflected, transmitted or diffracted by said object when it is struck by the said jet and the said beam of ultrasonic waves, the said coupling head comprising:

(a) a first tranquilization chamber connected to the output of said pump, (b) a second cylindrical tranquilization chamber connected to said first chamber by at least one channel for the passage of the liquid, (c) an ultrasonic transducer capable of emitting a beam of ultrasonic waves by means of an active surface, which is directed towards the object, said active surface being situated within the second chamber, centered on the axis of said second chamber and perpendicular to this axis, (d) a converging system coaxial with said second chamber and comprising an inlet connected to the said second chamber and of radius R1 at most equal to that of the said second chamber, and an outlet of radius R2 less than the radius R1 of the inlet and substantially equal to the radius selected by said jet, in which there have additionally been provided, within the second chamber, means for making the flow of liquid rectilinear, which means consist of a series of tubes which are parallel to the axis and which are disposed adjacent to one another.

It seems that this arrangement has not had the success which was foreseen, doubtless on account of the disturbances which appear at the inlet and at the outlet of the tubes which are parallel to the axis. Furthermore, this solution is costly and complicated.

It is, however, clear that the result would not be any better if this assembly of tubes were omitted.

The person skilled in the art might have in his mind the idea that the design of the interior of the coupling head might have an effect on the nature and the magnitude of the turbulence within the liquid.

In U.S. Pat. No. 3,908,445, the two tranquilization chambers are cylindrical and have different diameters, and are connected by radial ducts, and the connecting part of the converging system forms with the axis an angle which decreases progressively from approximately 45°, in contact with the second chamber, to 0°.

In U.S. Pat. No. 3,255,626, the connecting ducts are axial, and the second chamber is frustoconical and then cylindrical, while the connecting part is frustoconical.

In U.S. Pat. No. 4,403,510, the connecting ducts are oblique in relation to the axis, the second chamber is frustoconical, making an angle of approximately 30° with the axis, and it is connected directly to the outlet duct.

In U.S. Pat. No. 4,167,880, there is no first tranquilization chamber, and the sole tranquillization chamber, which contains the active surface of the transducer, is connected to the outlet duct by a simple shoulder perpendicular to the axis.

It is evident from this statement that the problem of the optimal internal shape of the orifice has not to date been clearly presented or resolved.

B. Gay et al., in the article entitled: "On the Design of the Contraction Section for a Wind Tunnel", Journal of Applied Mechanics" March 1973, presented a mathematical method of calculating the shape of the converging system of a tunnel through which air flows with a regulable pressure gradient, in the case of a flow in only two dimensions, the density being supposed to be constant.

The calculation was undertaken on the basis of a law of distribution of velocity along the axis:

$$f_1(x) = \alpha + \beta \int_0^x Z(x)dx + \gamma e^{-kx},$$

where $\alpha, \beta, \gamma$ and k are constants, and $$Z(x) = \frac{1}{\sqrt{2\pi}} e^{-x^2/2},$$

with the aid of a flow function:

$$\psi(x, y) = f_1(x) \cdot y + \ldots + f_{n+1}(x)y^{2n+1} + \ldots$$

where $$f_{(n+1)}(x) = -\frac{f''_n(x)}{2n(n+1)}.$$

The article by B. Gay et al. indicates that all the derivatives of the function $f_1(x)$ may be calculated in terms of Hermite polynomials:

$$f_1^{(n+1)}(x) = \beta Z^{(n)}(x) + \gamma \sqrt{2\pi} \; Z^{(n-1)}(x\sqrt{2k})\sqrt{2k^{n+1}}$$

where $Z^{(n)}(x) = (-1)^n H_n(x) Z(x)$.

The article by B. Gay et al. provides values of the constants $\alpha, \beta, \gamma$ and k which are suitable, in the case of the problem under investigation, to obtain a rapid contraction and a regular velocity gradient. Experience has shown that these values are not suitable for one of the problems which give rise to the present invention, which problem is that of determining the shape of a converging system capable of eliminating turbulence in the case of a liquid.

It should also be noted that, even if it were possible to deduce directly from this article the optimal shape of the converging system, that is to say of the connecting part between the second chamber and the outlet duct, this would not provide any indication regarding the structure of the remainder of the arrangement.

OBJECT OF THE INVENTION

The object of the invention is to provide an arrangement for the ultrasonic examination of objects in local immersion, which arrangement permits determination of defects with an accuracy and a certainty practically equal to those which are obtained with an arrangement operating in total immersion.

A further object of the invention is to provide such an arrangement which can readily and rapidly be adapted to the examination of objects having varying characteristics of shape, of nature, or of the nature of the defects under investigation.

SUMMARY OF THE INVENTION

The invention accordingly provides an arrangement for the ultrasonic investigation of an object by a local immersion technique, comprising:
a source of liquid,
a pump fed by said source,
a coupling head fed with liquid by said pump and capable of directing towards the object to be examined a jet of said liquid and a beam of ultrasonic waves contained in said jet and coaxial with this jet,
means sensitive to the ultrasonic waves reflected, transmitted or diffracted, by said object when it is struck by said jet and said beam of ultrasonic waves, said coupling head comprising:
(a) a first tranquilization chamber connected to the outlet of said pump,
(b) a second cylindrical tranquilization chamber connected to said first chamber by at least one channel for the passage of the liquid,
(c) an ultrasonic transducer capable of emitting a beam of ultrasonic waves by means of an active surface, which is directed towards the object, said active surface being situated in the second chamber, centered on the axis of said second chamber and perpendicular to this axis,
(d) a converging system coaxial with said second chamber and comprising an inlet connected to said second chamber and of width L1 at most equal to that of said second chamber, and an outlet of width L2 less than the width L1 of the inlet and substantially equal to the width selected by said jet, the shape of said converging system being substantially that which is obtained by a calculation in which a constant value is given to the expression:

$$Q(xy) = u_1(x) \cdot y + \ldots + u_{n+1}(x)y^{2n+1} + \ldots \quad (1)$$

where:

$$u_1(x) = \frac{a^2 + 1}{2a^2} + \frac{1 - a^2}{a^2} \int_0^x Z(x)dx$$

$$u_{n+1}(x) = \frac{-u_n''(x)}{2n(n+1)}$$

$$Z(x) = \frac{1}{\sqrt{2\pi}} e^{-x/2} \text{ and}$$

$$a = L2/L1$$

all the derivatives of $u_1(x)$ being calculated on the basis of Hermite polynomials $H_n(x)$ with $$u_1^{(n+1)}(x) = Z^{(n)}(x) \text{ and}$$

$$Z^{(n)}(x) = (-1)^n H_n(x) Z(x),$$

the calculations being undertaken for x=0 to x=1 when y=L2/2 after iterations; and the distance between the active surface of the transducer and the outlet of the converging system being such that said outlet is at the end of the Fresnel zone of the ultrasonic wave emitted by the transducer.

If the shape of the converging system is that of a surface of revolution, the widths L1 and L2 are equal to the diameters 2R1 and 2R2 at the inlet and outlet, but the invention is not limited to such a shape, and the transverse section of the converging system may be extended, for example so as to resemble an ellipse, in order to be adapted to a transducer the active surface of which is rectangular. In this case, the widths L1 and L2 must be measured in the same axial plane. The word "cylindrical" employed in the present text is applicable as well to shapes having a flattened section as to shapes having a circular section.

According to preferred embodiments:

The converging system is extended in the direction of the jet by a cylindrical end piece, of the same section as that of the outlet of the converging system and of a length determined by the fact that the surface of the object to be examined which is struck by the beam of ultrasonic waves is substantially at a maximum ultrasonic axial pressure defined by the transducer-converging system pair which is employed, and that the free passage of the jet of liquid between the end of said end piece and said surface of the object must be as short as possible, with due consideration being given to the operating conditions, the length of the end piece being moreover greater than four times its smaller width or its diameter.

The second tranquilization chamber is closed, on the object side, by a wall which is perpendicular to the axis and which carries a projection directed towards the interior of said chamber, this projection presenting a frustoconical axial aperture, the width of which decreases in progressing away from the chamber so as to connect up with the inlet of the converging system, either directly or by means of a cylindrical part having the same width as said inlet.

The end of the cylindrical end piece or of the converging system is adapted to avoid any dripping of water likely to disturb the jet and, preferably, for this purpose an annular groove is formed around said end.

The lateral wall of the second chamber and the converging system form part of an integral hollow body which is fixed in a sealed manner on the first chamber and which also includes, where these exist, the wall of the second chamber, the cylindrical part and the cylindrical end piece. In this case, according to a particularly advantageous embodiment, said hollow body is removably fixed on the first chamber, and there is provided a series of similar and interchangeable hollow bodies, each corresponding to a different acoustic pressure and/or ultrasonic frequency.

The walls of at least one of the chambers are constructed of transparent material, such as methyl polyacrylate, while at least the converging system and the connecting piece are constructed of a material which absorbs ultrasonic waves, such as polytetrafluoroethylene, or are internally coated with such a material.

The ducts connecting the first and second chambers are at least nine in number, and are disposed symmetrically, the ratio of their length to their diameter is at least equal to 4, each one of them exhibits within the first tranquilization chamber an inlet in the form of the mouth of a trumpet, and their respective axes are inclined to the axis of the chambers at an angle $\beta$ at least equal to 10 degrees.

The ultrasonic transducer is accommodated within the channel formed by a tubular sleeve axially traversing the first tranquilization chamber and by a bore in the wall which separates the two chambers, this being aligned with the said sleeve, the active surface of said transducer being disposed transversely to the axis $\alpha$ of the second tranquilization chamber in such a manner as to be in contact with the liquid which circulates there, and the bore in the wall is surrounded by a frustoconical neck, the angle at the vertex of which is for example approximately 60 degrees, and near to the base of which the ducts discharge.

The pump is an immersed vertical pump comprising a turbine with blades, an accumulator is inserted between the pump and the first tranquilization chamber, and the resonant frequency of this accumulator is adapted to the pulsation frequency of the blades of the turbine.

BRIEF DESCRIPTION OF THE DRAWINGS

The invention will be described in greater detail with reference to practical examples, which are non-limiting and which are illustrated with the aid of the Figures, in which:

FIG. 2 is a view, in axial section, of the coupling head of the arrangement of FIG. 1.

FIG. 3 is a diagrammatic view showing the position of certain parts of the coupling head in relation to the ultrasonic field.

FIGS. 4 to 9 are diagrams illustrating various profiles of the converging system of FIGS. 2 and 3.

FIG. 10 is a partial section, similar to FIG. 2, showing a different embodiment of the ducts joining the tranquilization chambers.

DETAILED DESCRIPTION OF THE INVENTION

Figure 1:
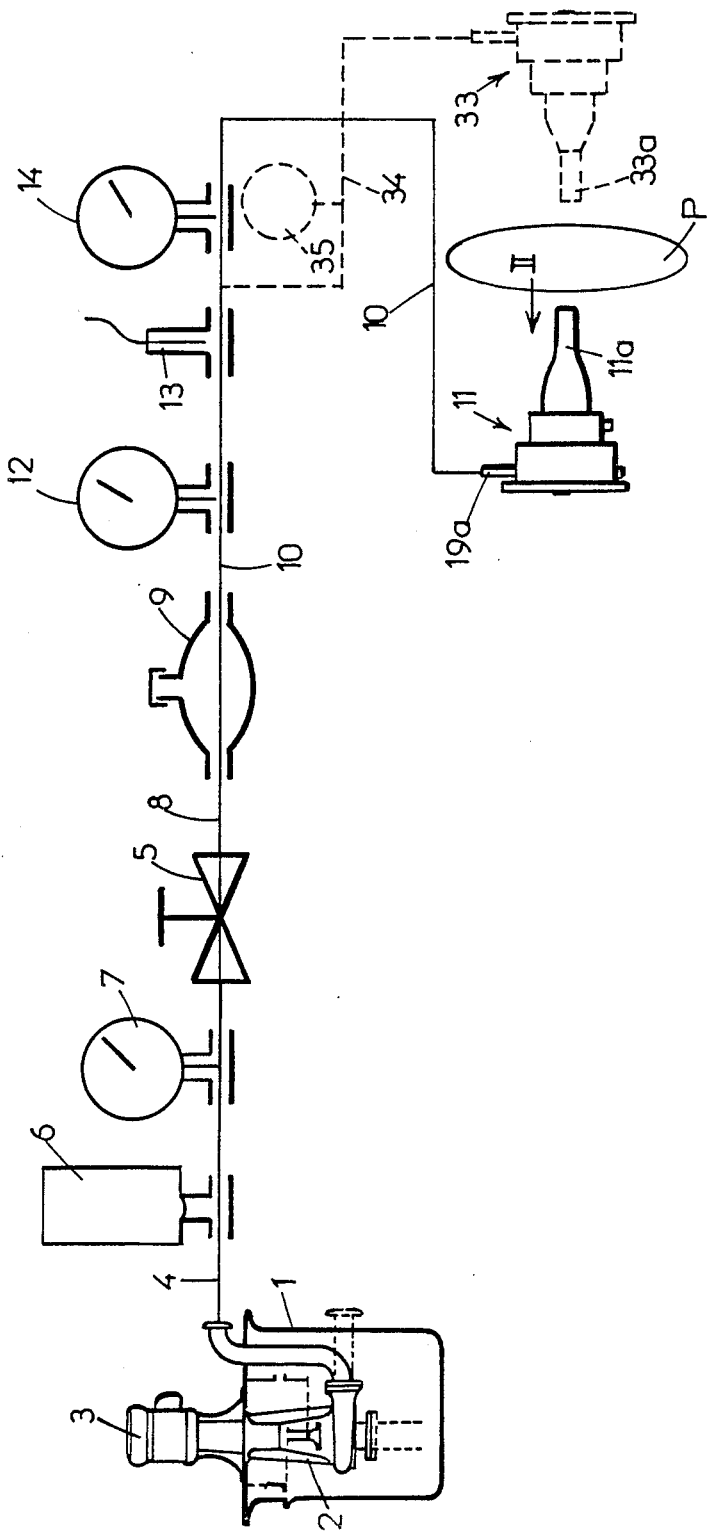
FIG. 1 is a schematic view of this embodiment.

The arrangement for the ultrasonic examination of objects in local immersion, which is schematically illustrated in FIG. 1, comprises in the first instance a cell 1, which is filled with water and in which there is entirely immersed a vertical pump 2, with a stuffing box or a mechanical seal, immersed in such a manner as to avoid any entry of air; what is involved is, for example, a pump comprising a turbine with blades which is driven at a constant speed of rotation by an electric motor 3. A tube 4 joins the lift of the pump 2 to the inlet of a throughput regulating valve, 5, which is advantageously of the oblique seating type. An accumulator 6 and a control manometer 7 are connected in parallel to the pipe 4, upstream of this valve 5. The accumulator 6 is of a current type, including for example a cushion of air separated from the liquid by a flexible membrane. Preferably, this accumulator 6 is dimensioned in such a manner that its resonant frequency is adapted to the pulsation frequency of the blades of the turbine of the pump 2. By virtue of this condition, there is a great reduction in the pressure fluctuations downstream of the accumulator 6, in the rhythm of the rotation of the turbine of the pump 2. This balancing of the pressure is improved as the accumulator 6 is located closer to the lift of the pump 2. The pressure value is adjusted by regulating the throughput with the aid of the regulating valve 5, the oblique seating of which reduces the generation of turbulence. A pipe 8 connects the outlet of the regulating valve 5 to the inlet of an air separator 9, or of a degassing device, which eliminates the last traces of gas which may have been entrained by the liquid. A pipe 10 connects the outlet of the air separator 9 to the inlet of a coupling head 11, one particularly advantageous embodiment of which will be described subsequently with reference to FIGS. 2 and 3. On this pipe 10 there are mounted, in parallel, a manometer 12 to monitor the outlet pressure, a pressure sensor 13 intended to generate, for example, an electrical signal proportional to the pressure within the pipe 10, and finally a flowmeter 14. It is finally seen from FIG. 1 that the coupling head 11 terminates in a cylindrical nozzle 11a, the end of which, from which a jet of water guiding a beam of ultrasonic waves emerges, as will be described subsequently in greater detail, is displaced, for example manually, or by known automatic means, which it is not necessary to describe, at a small distance from one of the external surfaces of the object P to be examined; in the zone of impact of the jet of water on the external surface of the object P, the ultrasonic waves penetrate to the interior of the latter and are reflected there by the internal defects of the latter, the detection of which is carried out on the basis of these reflections, according to well known processes which it is not necessary to describe.

In FIGS. 2 and 3, reference numeral 15 designates a component including a substantially plane flange 15a, and a cylindrical lateral wall 15b which, together with a concentric tubular sleeve 15c, delimits a first tranquillization chamber 16, which is annular and concentric with the tubular sleeve 15c. Reference numeral 17 designates a plate which is supported on the ends of the wall 15b and of the sleeve 15c so as to close the chamber 16. The component 15 and the plate 17 are advantageously constructed of a transparent material such as polymethacrylate, so as to permit visual inspection for the absence of bubbles in the chamber 16. The plate 17 is fixed to the component 15 by screws 18. It may also be fixed by adhesion. The lateral wall 15b of the first tranquilization chamber 16 is traversed by a number, which is at least equal to three, of radial ducts, only one of which, 19a, is shown in FIG. 2, which are fed by a distributor, not shown, from the end of the pipe 10 (FIG. 1) closest to the coupling head 11. The radial feeding ducts, such as 19a to 19c, are preferably disposed in a regular manner around the cylindrical wall 15b, as can be seen in FIG. 2. The wall 17 is traversed by at least 9 ducts 20 having a ratio of length to diameter of at least 4, and preferably disposed symmetrically about the common axis of the cylindrical wall 15b and of the tubular sleeve 15c. Each duct 20 has, within the first tranquilization chamber 16, an inlet 20a in the form of the mouth of a trumpet, and its axis is inclined to the axis of the head 11 at an angle β which is at least equal to 10 degrees. On the other hand, an ultrasonic emitter-receiver 28, which is of a known type and which it is not necessary to describe in detail, has its cylindrical casing embedded within the tubular sleeve 15c of the component 15, in such a manner that its active surface 28a is disposed transversely to the axis, at the outlet, within the second tranquilization chamber 24, of a bore 17a which extends, through the wall 17, the internal channel of the tubular sleeve 15c. In this embodiment, the bore 17a of the wall 17 is surrounded by a frustoconical neck 17b, the angle of which at the vertex is, for example, approximately 60 degrees, and close to the base of which the ducts 20 discharge.

On the web 17, on the side opposite to the first tranquilization chamber, there is fixed with the aid of screws 21 a hollow body of revolution about the axis of the head, with the interposition of a sealing point 22. This hollow body includes a cylindrical part 23 which defines, together with the web 17 and another wall 24a perpendicular to the axis, a second tranquilization chamber 24, into which the ducts 20 discharge. The wall 24a carries a projection 24b which is directed towards the interior of the said chamber. This projection has a frustoconical axial aperture 24c, the diameter of which decreases as it gets further from the chamber 24, and which is connected to a cylindrical part 25 which, in turn, forms part of the hollow body. The height of the projection 24b is approximately 15% of the axial length of the chamber 24.

The cylindrical part 25 is extended by a converging system 26, the radius R1 of which at its inlet 26a is the same as that of the cylindrical part 25.

The shape of this converging system and its position are very important elements of the invention, and will be described in greater detail.

The course of the converging system must be such that the flow of the liquid therein is as regular as possible, with the minimum of eddies capable of partially diffracting the sound energy.

The work undertaken by the inventors has enabled it to be established that this result is obtained when the course of the internal surface of the converging system 26 is that which results from the calculation indicated hereinabove.

This calculation emerges from an extrapolation from the article by Gay et al. to which reference was made hereinabove.

It is inferred from Formulae (2) and (3) on page 309 of the same article that the axial velocity of a fluid flowing in a converging system is given by the equation:

$$u_{1(x)} = \alpha + \beta \int_0^l \frac{e^{-x^2}}{\sqrt{2\pi}} dx + \gamma e^{-kx^3},$$

where $u_1$ designates the velocity of the fluid along the axis, x designates the distance from the current point to the inlet of the converging system and l designates the length of the converging system.

This relation permits calculation of an approximate value of the current function $\psi(x, y)$ at the current point (y being the distance from this point to the axis), by virtue of the following series expansion:

$$\psi(xy) = u_1(x)y + \ldots + u_{n+1}(x)y^{2n+1} + \ldots$$

with $$u_{n+1}(x) = \frac{u_n''(x)}{2n(2n+1)}.$$

These equations are inferred from equations (1) and (2), which appear at the head of the article mentioned hereinabove.

The optimal profile of the converging system is clearly selected in order that a generatrix of the wall of the converging system should coincide with a liquid flow line.

The studies and experiments undertaken by the inventors have shown that, with the values of the constants α, β, γ and k given in the above cited article, it was not possible to obtain a converging system giving the desired result, that is to say a minimum of eddies capable of disturbing the ultrasonic beam, but that by giving satisfactory values to the constants $\alpha$, $\beta$ and $\gamma$ it was possible to obtain with the same principle of calculation, a suitable result. These values are:

$$\alpha = \frac{a^2 + 1}{2a^2}; \beta = \frac{1 - a^2}{a^2}; \gamma = 0$$

with $a = L2/L1$; a is the contraction ratio, which is equal to the ratio of the inlet and outlet radii (R1, R2) of the converging system when the latter is generated by revolution.

These values, when transposed in the equations of the Gay et al. article, result in those which have been given hereinabove, and permit, by means of an appropriate computer program, tracing of the flowlines and of the families of profiles of the converging system, for example for various values of R2 either with R1 constant or with a=R2/R1 constant. These forms of profiles of the converging system ensure a minimum of disturbances within the converging system and an outlet velocity of the latter which is as uniform as possible.

FIGS. 4 to 9 of the accompanying drawing are diagrams, using the x and y coordinates previously defined, which represent five possible profiles of the converging system according to the present invention.

The abscissae which have been indicated therein are the values of l corresponding to the various pairs of values of the radii R1 and R2. The comparison, for example, of FIGS. 7 and 8 shows that, for a particular outlet radius R2=5 mm, l equals 52 mm if R1=9 mm and l=100 mm if R1=17 mm.

The work undertaken by the inventors has also related to the propagation of ultrasonic waves through a liquid flow comprising a converging system followed by a substantially cylindrical part.

FIG. 3 includes a curve C which shows the fluctuations of the axial ultrasonic pressure under these conditions, which are different from those which are observed in an indefinite medium, along the axis of the beam.

Starting from the emitter 28a, which is assumed to be flat, the ultrasonic pressure includes, a first zone A referred to as the "near field", or "Fresnel zone", in which the ultrasonic pressure exhibits rapid variations, and a second zone B, referred to as the "far field", in which the variations are far more attenuated. The length of the near field zone is also designated as the "focal distance f" of the emitter if the latter is of the type referred to as "focussed".

The boundary between the two zones corresponds to a maximum pressure M1, which constitutes the end of the Fresnel zone, and other pressure maxima M2, M3, etc . . . are located in succession. The precise origin of the maxima M2, M3 is not yet clearly established, but the inventors have found that the best results are obtained when the outlet 26b of the converging system coincides with the maximum M1 which marks the end of the Fresnel zone, and when the point of impact of the ultrasonic beam on the object to be examined is situated on the first, M2, or second, M3, of the following maxima. In FIG. 10, P and then P' thus represent the two best possible positions. The reason why more distant maxima (not shown) are not preferred is essentially the increasing intensity of the disturbances due to eddies.

The choice of R1 and R2 depends on the throughput of liquid and on its viscosity. There is a minimum value of R1 for each throughput which corresponds to a maximum velocity not to be exceeded in the cylindrical part 25 in order to obtain a regular flow of liquid, and the value of R2 depends, on the one hand, on the form of the defects to be detected and more generally on the nature of the object to be examined and, on the other hand, for a given throughput, on the velocity to be obtained for the jet.

Beyond the outlet 26b of the converging system, the hollow body is again extended by a cylindrical end piece 27, which has the same radius R2. The function of this connecting piece is to protect the jet from contact with the atmosphere and from the disturbances which result therefrom, up to a location in the vicinity of the surface of the object to be examined.

The length of the end piece 27 is preferably at least equal to four times its diameter, or, if it has a flattened section, its smallest width, for effective stabilization of the velocities after the converging system. On the other hand, it must be sufficiently long to protect the jet from the external disturbances and to prevent inflection of the jet under the influence of a displacement of the latter in circumstances in which the process is carried out by displacing the jet in relation to the object to be examined. In this connection, it will be noted that, although the figures appear to demonstrate that the axis of the jet is horizontal, it is in general preferable that it should be vertical, in order to avoid inflection under the influence of gravity. In another respect, the end piece must be sufficiently short to permit satisfactory escape of the projected liquid and to avoid any risk of shock between the end piece and the object to be examined in the course of their respective displacements.

The outlet 29 of the cylindrical duct 27 of the said orifice is adapted to avoid, above all when it is placed vertically, any dripping of water which may disturb the jet; to this end, an annular groove 29a is formed around the outlet 29 of the duct 27. Arrangements are provided to clear the liquid circulating in the chambers 16 and 24 of air bubbles which it entrains; the arrangements concerned comprise clearing screws 30 and 31.

As has been stated, the lateral walls of the chamber 24, its frontal wall 24a, the cylindrical part 25, the converging system 26 and the end piece 27 form part of a single hollow body, which is fixed in a removable manner, by screws 21, on the plate 17.

Although a single hollow body is shown, the reader will be aware that the arrangement, in order to be adapted to varying conditions of examination, is equipped with a set of interchangeable hollow bodies. In fact, depending upon the nature and the form of the defects to be detected, or their number, it will be necessary to have various jets of width L2. The velocity of the jet must be selected as a function, in particular, of the relative velocity of displacement of the coupling head and of the objects to be examined, and of the vertical or horizontal orientation of the jet. These data determine the throughput, and consequently the value of L1 and the shape of the converging system; this, in turn, influences the acoustic characteristics of the entire system for a given transducer, and thus the position of the outlet of the converging system and the length of the connecting piece. Conditions concerning properties of the material of which the object to be examined is constructed, and indeed the nature of the defects, make it necessary to provide for the use of a plurality of transducers having different frequencies. The structure of the components 15 and 17 permits the easy exchange of one transducer for another, but such exchange will involve a change of hollow body, for the reasons set forth hereinabove.

It will be noted that, in an arrangement including interchangeable hollow bodies providing jets of varying diameters, the flowmeter 14 and the flow regulating valve 5 are essential accessory components. In fact, each hollow body is associated with a well-defined throughput, in order to obtain the best measurement results.

In the embodiment represented, the hollow body is constructed of polytetrafluoroethylene, a product which exhibits strong acoustic absorption. It may be constructed of a different material, preferably also having strong acoustic absorption. This property plays a part in the determination of the shape of the hollow body, in view of the fact that it has an influence on the propagation of the ultrasonic waves.

The pipe 10 (FIG. 1) and the distributor (not shown) supply the first tranquilization chamber 16, via the three radial ducts 19a to 19c, with currents of water, the flowrate of which is determined with precision, and the pressure of which is subject to practically negligible fluctuations, and which entrain practically no air or gas bubbles. By reason of the symmetrical arrangement of the supply ducts 19a to 19c, there is produced within the first tranquilization chamber 16 a very regular flow, which feeds the second tranquilization chamber 24, via the ducts 20 which are likewise disposed in a symmetrical manner about the axis, in such a way that a very regular flow is likewise established within this second tranquilization chamber. It is within this chamber 24 that the ultrasonic waves generated by the active surface 28a of the emitter 28 begin to propagate within the mentioned flow, and then within the flow, which is likewise regular and only slightly turbulent and which, on leaving the said chamber 24, then traverses the orifice 25, 26 and 27 of the orifice, in order to form, at the outlet 29, a jet which is directed towards the object to be examined P, which is placed at a maximum of axial ultrasonic pressure, as is schematically illustrated in FIG. 1. Throughout the entire flow of the liquid, more especially of the water, within the second tranquilization chamber 24, as well as within the components 25, 26 and 27 of the orifice, the beam of ultrasonic waves undergoes no more than very slight diffraction, as a result of the very small quantities of air or of gas which are entrained by the liquid, and the greater part of the ultrasonic energy is propagated in the direction of the axis, towards the right in FIG. 3, as a result of the regular flow, exhibiting only slight turbulence, of the liquid. As, moreover, the pressure of the latter remains very substantially constant, the part of the jet leaving the nozzle 27 at 29, which strikes the peripheral surface of the object to be examined P, exhibits a high level of stability, which ensures transmission with a high output level of the ultrasonic energy to the object P. The ultrasonic waves reflected by the internal defects of the object P leave the latter by the surface thereof, on which the jet of water is directed, and the latter then guides them towards the transducer 28, which also functions as a receiver.

FIG. 1 shows, in broken lines, a second head 33 provided with a nozzle 33a to project a second jet of liquid onto the zone of the object P which is being examined from which there emerge the ultrasonic waves transmitted through the said object P from the first jet projected by the head 11. The second head 33, which may be identical to the first head 11, does however include a receiver for the ultrasonic waves which have been emitted by the emitter of the said head 11, and which have traversed the object P from one side to the other. The second head 33 may be supplied with liquid by means of a branch 34 of the hydraulic circuit beyond the sensor 13, this branch including a flowmeter 35.

FIG. 10 shows a variant of the shape of the inlet of the ducts 20. According to this variant, the neck 20a, which has the shape of the mouth of a trumpet, projects in relation to the wall 17 which closes the first tranquilization chamber 16 and extends in a forward direction as far as the vicinity of the middle of the length of this chamber. This form, which is slightly more complicated that that of FIG. 2, reduces the turbulence to an even greater extent, above all in the case of large throughputs.

We claim:

1. An apparatus for the ultrasonic examination of an object by a local immersion technique, comprising:
   container means containing a liquid;
   a coupling head capable of directing towards an object to be examined a jet of said liquid and a beam of ultrasonic waves which is contained in said jet of liquid and is coaxial with said jet of liquid, said coupling head comprising:
   (a) a first tranquilization chamber,
   (b) a second cylindrical tranquilization chamber connected to said first chamber by at least one channel for the passage of said liquid, said second cylindrical tranquilization chamber having a width,
   (c) an ultrasonic transducer capable of emitting a beam of ultrasonic waves towards said object, said ultrasonic transducer including an active surface which is situated within said second chamber and is centered on the axis of said second chamber, said active surface being perpendicular to said axis,
   (d) a converging system coaxial with said second chamber and comprising an inlet connected to said second chamber and of a width $L_1$, which is at most equal to said width of said second chamber, and an outlet of a width $L_2$, which is less than the width $L_1$ and is substantially equal to the width selected for said jet, the shape of said converging system being substantially that which is obtained by a calculation in which a constant value is given to the expression:

$$Q(xy) = u_1(x) \cdot y + \ldots + u_{n+1}(x) y^{2n+1} + \ldots \quad (1)$$

where:

$$u_1(x) = \frac{a^2 + 1}{2a^2} + \frac{1 - a^2}{a^2} \int_0^x Z(x) dx$$

$$u_{n+1}(x) = \frac{-u_n''(x)}{2n(n+1)}$$

$$Z(x) = \frac{1}{\sqrt{2\pi}} e^{-x/2} \text{ and}$$

$$a = L2/L1$$

all the derivatives of $u_1(x)$ being calculated on the basis of Hermite polynomials $H_n(x)$ with $u_1^{(n+1)}(x) = Z^{(n)}(x)$ and $Z^{(n)}(x) = (-1)^n E_n(x) Z(x)$, the calculation being undertaken for x=0 to x=1 when y=L$_2$/2 after iterations; and the distance between the active surface of said transducer and said outlet of the converging system being such that said outlet is at the outlet of the Fresnel zone of the ultrasonic wave emitted by the transducer;

a pump means for conveying liquid from said container means to the first tranquilization chamber of said coupling head; and means sensitive to the ultrasonic waves reflected, transmitted or diffracted by said object when it is struck by said jet of liquid and said beam of ultrasonic waves.

2. An apparatus according to claim 1, wherein said converging system is extended in the direction of said jet by a cylindrical end piece having the same section as that of said outlet of said converging system and of a length determined by the fact that the surface of the object to be examined which is struck by the beam of ultrasonic waves must be situated at a maximum ultrasonic axial pressure defined by the transducer-converging system pair which is employed, and wherein the free passage of said jet of liquid between the end of said end piece and said surface of the object must be as short as possible, with due consideration being given to the operating conditions, the length of said end piece being moreover at least equal to four times its greatest width or its diameter.

3. An apparatus according to claim 1, wherein said second tranquilization chamber is closed on the object side by a wall which is perpendicular to said axis and which carries a projection directed towards the interior of said chamber, this projection presenting an axial aperture, the diameter of which decreases in progressing away from said chamber so as to connect up with said inlet of said converging system, either directly or by means of a cylindrical part having the same diameter as said inlet.

4. An apparatus according to claim 1, wherein the end of said cylindrical end piece or of the converging system is adapted to avoid any dripping of liquid likely to disturb the jet.

5. An apparatus according to claim 4, wherein, in order to avoid any dripping of liquid, an annular groove is formed around said outlet.

6. An apparatus according to claim 1, wherein the lateral wall of the second chamber and the converging system form part of an integral hollow body which is fixed in a sealed manner on the first chamber.

7. An apparatus according to claim 2, wherein said lateral wall of said second tranquilization chamber, said converging system and said end piece form part of an integral hollow body which is fixed, in a sealed manner, on said first tranquilization chamber.

8. An apparatus according to claim 3, wherein said lateral wall and said wall perpendicular to the axis of said second tranquilization chamber form part of an integral hollow body which is fixed in a sealed manner on said first tranquilization chamber.

9. An apparatus according to claim 6, wherein said hollow body is removably fixed on said first chamber, and including a series of similar and interchangeable hollow bodies, each corresponding to a different acoustic pressure and/or ultrasonic frequency.

10. An apparatus according to claim 7, wherein said hollow body is removably fixed on said first chamber, and including a series of similar and interchangeable hollow bodies, each corresponding to a different acoustic pressure and/or ultrasonic frequency.

11. An apparatus according to claim 8, wherein said hollow body is removably fixed on said first chamber, and including a series of similar and interchangeable hollow bodies, each corresponding to a different acoustic pressure and/or ultrasonic frequency.

12. An apparatus according to claim 2, wherein the walls of at least one of said chambers are made of methyl polyacrylate, and wherein said end piece is made of polytetrafluoroethylene.

13. An apparatus according to claim 1, wherein said channels connecting said first and second tranquilization chambers are at least nine in number and are disposed symmetrically, the ratio of their length to their diameter being at least equal to 4, each one of said channels exhibiting within the first tranquilization chamber an inlet in the form of the mouth of a trumpet, and having their respective axes are inclined to the axis at an angle at least equal to 10 degrees.

14. An apparatus according to claim 1, wherein said ultrasonic transducer is accomodated within the channel formed by a tubular sleeve axially traversing said first tranquilization chamber and by a bore in the wall which separates the two chambers, being aligned with the said sleeve, the active surface of said transducer being disposed transversely to the axis of said second tranquilization chamber in such a manner as to be in contact with the liquid which circulates there, the bore in the wall being surrounded by a frustonical neck, the angle at the vertex of which approximately 60 degrees, and near to the base of which said channels connecting said first and second tranquilization chambers discharge.

15. An apparatus according to claim 1, wherein said pump means is an immersed vertical pump comprising a turbine with blades, wherein an accumulator is inserted between said pump and said first tranquilization chamber, and wherein the resonant frequency of this accumulator is adapted to the pulsation frequency of the blades of the turbine.

16. A coupling head for ultrasonic examination by a local immersion technique, comprising:
(a) a first tranquilization chamber connectable to the outlet of a pump,
(b) a second cylindrical tranquilization chamber connected to said first tranquilization chamber by at least one channel for the passage of liquid, said second cylindrical tranquilization chamber having a width,
(c) an ultrasonic transducer capable of emitting a beam of ultrasonic waves towards an object, said ultrasonic transducer including an active surface which is situated in said second chamber and is centered on the axis of said second chamber, said active surface being perpendicular to said axis,
(d) a converging system coaxial with said second chamber and comprising an inlet connected to said second chamber and of a width L$_1$, which is at most equal to said width of said second chamber, and an outlet of a width L$_2$, which is less than the width L$_1$ and is substantially equal to the width selected for said jet, the shape of said converging system being substantially that which is obtained by a calculation in which a constant value is given to the expression:

$$Q(xy) = u_1(x) \cdot y + \ldots + u_{n+1}(x) y^{2n+1} + \ldots \quad (1)$$

where:

$$u_1(x) = \frac{a^2+1}{2a^2} + \frac{1-a^2}{a^2} \int_0^x Z(x)dx$$

$$u_{n+1}(x) = \frac{-u_n''(x)}{2n(n+1)}$$

$$Z(x) = \frac{1}{\sqrt{2\pi}} e^{-x/2} \text{ and}$$

$$a = L_2/L_1$$

all the derivatives of $u_1(x)$ being calculated on the basis of Hermite polynomials $H_n(x)$ with $$u_1^{(n+1)}(x) = Z^{(n)}(x) \text{ and}$$

$$Z^{(n)}(x) = (-1)^n E_n(x) Z(x),$$

the calculation being undertaken for $x=0$ to $x=1$ when $y=L_2/2$ after iterations; and the distance between the active surface of the transducer and the outlet of said converging system being such that said outlet is at the outlet of the Fresnel zone of the ultrasonic wave emitted by the transducer.

17. A coupling head according to claim 16, wherein said converging system is extended in the direction of the jet by a cylindrical end piece having the same section as that of the outlet of said converging system and of a length determined by the fact that the surface of said object to be examined which is struck by said beam of ultrasonic waves must be situated at a maximum ultrasonic axial pressure defined by the transducer-converging system pair which is employed, and wherein the free passage of the jet of liquid between the end of said end piece and said surface of said object must be as short as possible, with due consideration being given to the operating conditions, the length of the end piece beinbg moreover at least equal to four times its greatest width or its diameter.

18. A coupling head according to claim 16, wherein said second tranquilization chamber is closed, on the object side, by a wall which is perpendicular to the axis and which carries a projection directed towards the interior of said chamber, said projection presenting an axial aperture, the diameter of which decreases in progressing away from the chamber so as to connect up with the inlet of said converging system, either directly or by means of a cylindrical part having the same diameter as said inlet.

* * * * *

UNITED STATES PATENT AND TRADEMARK OFFICE
CERTIFICATE OF CORRECTION

PATENT NO. : 4,726,231
DATED : February 23, 1988
INVENTOR(S) : Hervé Tretout et al.

It is certified that error appears in the above-identified patent and that said Letters Patent is hereby corrected as shown below: On the title page Insert -- [73] Assignee: Avions Marcel Dassault-Breguet Aviation, Vaucresson, France --

Signed and Sealed this

Twenty-seventh Day of September, 1988

*Attest:*

DONALD J. QUIGG

*Attesting Officer*  *Commissioner of Patents and Trademarks*